United States Patent [19] [11] Patent Number: 6,051,124
Aoki [45] Date of Patent: Apr. 18, 2000

[54] ZETA-POTENTIAL DETERMINING APPARATUS

[75] Inventor: Hidemitsu Aoki, Tokyo, Japan

[73] Assignee: NEC Corporation, Tokyo, Japan

[21] Appl. No.: 08/942,137

[22] Filed: Sep. 29, 1997

[30] Foreign Application Priority Data

Sep. 27, 1996 [JP] Japan ................................ 8-256914

[51] Int. Cl.[7] .................................................. G01N 27/26
[52] U.S. Cl. ........................................................ 204/600
[58] Field of Search ......................... 73/861.08, 861.02, 73/53.01; 356/337, 344; 204/450, 461, 600, 612, 606; 261/1, 2; 210/656

[56] References Cited

U.S. PATENT DOCUMENTS 4,219,395  8/1980  Smith et al. .
4,617,104  10/1986  Kawai et al. ........................ 204/645
5,358,618  10/1994  Ewing et al. .

FOREIGN PATENT DOCUMENTS 63-200052  8/1988  Japan .
7-239313   9/1995  Japan .
8-128985   5/1996  Japan .

OTHER PUBLICATIONS

Pp. 205 and 520 of Webster's II New Riverside University Dictionary, 1994.
Cole et al. ("Free–solution electrophoresis of proteins in an improved density gradient column and by capillary electrophoresis", J. Chromatogr. A 707 (1995) Month Unknown 77–85).
F. Kitahara et al., "Various Measuring Method of Zeta Electric Potential", pp. 52–53 and 68–71, Zeta Electronic Potential, 1995 Month Unknown (with English Abstract).

*Primary Examiner*—Jill Warden
*Assistant Examiner*—Alex Noguerola
*Attorney, Agent, or Firm*—Young & Thompson

[57] ABSTRACT

A zeta-potential determining apparatus that determines accurately a zeta potential of a solution with a tendency to generate bubbles due to an applied electric field. This apparatus includes a cell member having a cavity, and positive and negative electrodes located in the cavity. The cell member further has first and second bubble-barrier membranes in vicinities of the positive and negative electrodes. Each of the first and second bubble-barrier membranes blocks bubbles generated in the solution in the vicinity of the corresponding electrodes. Each of the first and second bubble-barrier membranes also allows ions contained in the solution to penetrate therethrough. In use, a dc voltage is applied across the positive and negative electrodes. A solution containing charged monitor particles is supplied and stored in the cavity of the cell member.

1 Claim, 5 Drawing Sheets

ZETA-POTENTIAL DETERMINING APPARATUS

BACKGROUND OF THE INVENTION

1. Field of the Invention

The present invention relates to a zeta-potential determining apparatus and more particularly, to a zeta-potential (i.e., electrokinetic potential) determining apparatus that is applicable to monitoring of the performance of a cleaning or rinsing solution in manufacturing of precision industrial products including semiconductor integrated circuits (ICs).

2. Description of the Prior Art

In recent years, the integration scale or level in the technology of precision industrial products, particularly ICs, has been progressing remarkably. To continuously provide the manufacturing processes of these products with higher cleanliness, it is required to enhance the performance of cleaning and rinsing solutions.

Determination of a zeta ($\zeta$) potential or electrokinetic potential allows us to know whether the contaminant particles included in a cleaning or rinsing solution for a semiconductor substrate tend to be deposited on the substrate or not. Thus, the zeta-potential determination plays an important role in controlling the performance of cleaning and rinsing solutions in the IC manufacturing technology.

Generally, a particle is not in the electrically neutral state, and it is usually charged positively or negatively. When an external electric field is applied to a liquid electrolyte in which charged particles are dispersed, these particles are moved according to the sign (or, polarity) and magnitude of the charge of the particles in the electrolyte. This phenomena that charged particles contained in a solution are moved by an applied electric field has been known as the "electrophoresis".

If monitor particles, i.e., charged particles for monitoring the mobility, are diffused into a solution and then, the mobility of these monitor particles is measured, a "zeta potential" can be calculated from the measured mobility. The zeta potential is defined as an electric potential generated between the outermost layer of the monitor particle and the solution.

For example, when negatively charged particles of polystyrene latex (PSL) are dispersed in a solution and an electric field is applied across positive and negative electrodes placed apart from one another in the solution, the particles will move toward the positive electrode.

FIG. 1 is a schematic cross-sectional view showing the outline of a cell member of a conventional zeta-potential determining apparatus.

In FIG. 1, a cap 51, which is made of quartz, has a cross section of an inverted U-shape. The cap 51 has a top wall and two opposing side walls. The bottom and the remaining two sides are opened. A bottom plate 52, which is made of quartz, is attached to the opening bottom of the cap 51. Plate-shaped positive and negative electrodes 55 and 56, each of which is made of platinum (Pt), are attached to the two opening sides of the cap 51, respectively. Thus, a cavity 58 of the cell member, which has a shape of a rectangular parallelepiped, is defined by the cap 51, the bottom plate 52, and the positive and negative electrodes 55 and 56.

On measurement or determination, a solution 53, in which negatively-charged monitoring particles 54 such as PSL particles are suspended, is placed or stored in the cavity 58 of the cell member. Then, an appropriate dc voltage is applied across the positive and negative electrodes 55 and 56, thereby moving the monitoring particles 54 in the solution 53, as shown by an arrow in FIG. 1. The mobility of the moving monitor particles 54 is measured in this state.

In recent years, the primary method of measuring the mobility of the monitor particle 54 has been to irradiate a laser beam into the solution 53 from the outside and to determine the mobility utilizing the laser Doppler effect resulting from the motion of the particles 54.

Specifically, as shown in FIG. 2, an incident laser beam L1, which is emitted from a laser oscillator or laser-beam source 101 located outside the cell member, is irradiated to the solution 53 in the cavity 58. The incident laser beam L1 is reflected by the monitor particles 4 to generate a reflected laser beam L2. The reflected laser beam L2 is detected by an optical detector 102 located outside the cell member.

Because the monitor particles 54 are moved in the solution 53 due to the electrophoresis phenomenon, a frequency difference is produced between the incident and reflected laser beams L1 and L2. A data processor 103 performs a frequency analysis using the frequency difference between the two beams L1 and L2, in which a beat frequency is generated by mixing the two frequencies of the beams L1 and L2 and then, the mobility of the monitor particle 54 in the solution 53 is determined from the beat frequency. Further, the data processor 103 calculates a zeta potential based on the determined mobility of the particles 54.

With the conventional zeta-potential determining apparatus shown in FIG. 1, it has been difficult to determine a zeta potential for the solution 53 when the solution 53 has a tendency of generating bubbles 57 in the vicinities of the positive and negative electrodes 55 and 56 due to the applied dc voltage. This is because the moving monitor particles 54 in the solution 53 cannot be distinguished from the bubbles 57 by the laser beams L1 and L2.

In particular, many of the solutions that have been used for cleaning or rinsing a semiconductor substrate in the IC manufacturing technology contain hydrogen peroxide ($H_2O_2$). Thus, if an electric field is applied to any one of these solutions, a number of bubbles will be generated in the vicinities of the positive and negative electrodes 55 and 56. Therefore, it is difficult to determine a zeta potential for any of the cleaning solutions, such as a mixed solution (APM) of ammonia ($NH_3$) and hydrogen peroxide ($H_2O_2$), a mixed solution (HPM) of hydrochloric acid (HCl) and hydrogen peroxide, a mixed solution (SPM) of sulfuric acid ($H_2SO_4$) and hydrogen peroxide, and a mixed solution (FPM) of hydrofluoric acid (HF) and hydrogen peroxide.

SUMMARY OF THE INVENTION

Accordingly, an object of the present invention is to provide a zeta-potential determining apparatus that determines accurately a zeta potential of a solution that has a tendency to generate bubbles due to an applied electric field.

Another object of the present invention is to provide a zeta-potential determining apparatus that can be used for monitoring the performance of a cleaning or rinsing solution with a tendency to generate bubbles due to an applied electric field.

The above objects together with others not specifically mentioned will become clear to those skilled in the art from the following description.

A zeta-potential determining apparatus according to the present invention is comprised of a cell member having a cavity, a positive electrode, and a negative electrode. The positive and negative electrodes are located in the cavity to be apart from one another.

The cell member further has a first portion for receiving a first bubble-barrier membrane in a vicinity of the positive electrode and a second portion for receiving a second bubble-barrier membrane in a vicinity of the negative electrode.

The first bubble-barrier membrane has a property of blocking bubbles generated in the solution in the vicinity of the positive electrode that move toward the negative electrode. The first bubble-barrier membrane has another property of allowing ions contained in the solution to penetrate through the first bubble-barrier membrane.

Similarly, the second bubble-barrier membrane has a property of blocking bubbles generated in the solution in the vicinity of the negative electrode that move toward the positive electrode. The second bubble-barrier membrane has another property of allowing the ions contained in the solution to penetrate through the second bubble-barrier membrane.

On use, the first and second bubble-barrier membranes are placed in the first and second portions, respectively. A dc voltage is applied across the positive and negative electrodes. A solution containing charged monitor particles is supplied and stored in the cavity of the cell member.

With the zeta-potential determining apparatus according to the present invention, the first bubble-barrier membrane is placed in the first portion of the cell member in the vicinity of the positive electrode and the second bubble-barrier membrane is placed in the second portion of the cell member in the vicinity of the negative electrode on use (i.e., on zeta-potential determination). The first bubble-barrier membrane has the property of blocking bubbles generated in the solution in the vicinity of the positive electrode that move toward the negative electrode. The second bubble-barrier membrane has the property of blocking bubbles generated in the solution in the vicinity of the negative electrode that move toward the positive electrode.

Accordingly, the bubbles in the solution do not enter an intervening region between the first and second portions of the cell member. This means that the bubbles are prevented from existing in the intervening region On the other hand, each of the first and second bubble-barrier membranes has the property of allowing the ions contained in the solution to penetrate through a corresponding one of the first and second bubble-barrier membranes. Therefore, a sufficient electric current may flow through the solution according to the applied dc voltage, and thus, the monitor particles in the solution may be moved in the solution due to the electrophoresis phenomenon.

This means that a zeta-potential is able to be determined accurately even if the solution has a tendency to generate bubbles due to an applied electric field.

As a result, this zeta-potential determining apparatus can be used for monitoring the performance of a cleaning or rinsing solution with a tendency of generating bubbles due to an applied electric field.

In a preferred embodiment of the apparatus according to the present invention, the cell member has first and second holes for discharging the bubbles in the solution to the outside near the first and second portions, respectively. There is an additional advantage that the determination or measurement is more difficult to be affected by the bubbles.

In another preferred embodiment of the apparatus according the present invention, each of the first and second bubble-barrier membranes is made of an ion-exchange membrane or porous membrane such as a filter paper.

BRIEF DESCRIPTION OF THE DRAWINGS

In order that the present invention may be readily carried into effect, it will now be described with reference to the accompanying drawings.

DETAILED DESCRIPTION OF THE PREFERRED EMBODIMENTS

Preferred embodiments of the present invention will be described below with reference to the drawings attached.

First Embodiment

A zeta-potential determining apparatus according to a first embodiment of the present invention is shown in FIGS. 3 to 6. This apparatus is comprised of a cap 1, a bottom plate 2, a supporting member 13, and a cell block 14. The cap 1 and the bottom plate 2 constitute a cell member.

Figure 3:
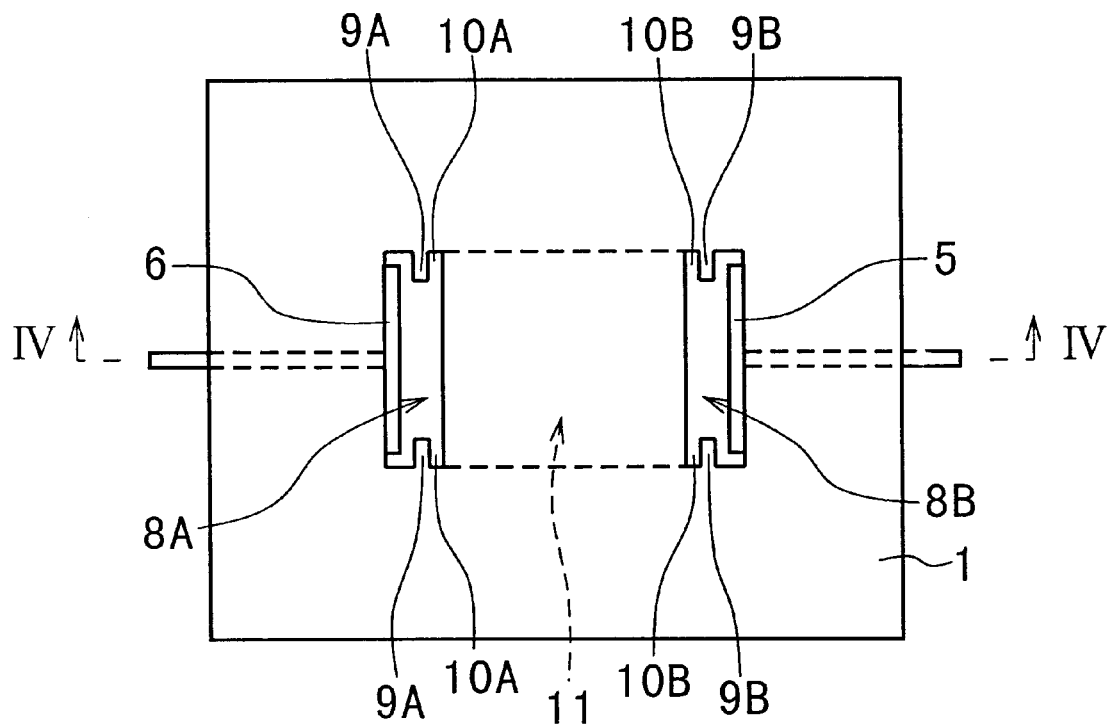
FIG. 3 is a schematic plan view of a cell member of a zeta-potential determining apparatus according to a first embodiment of the present invention.
Figure 4:
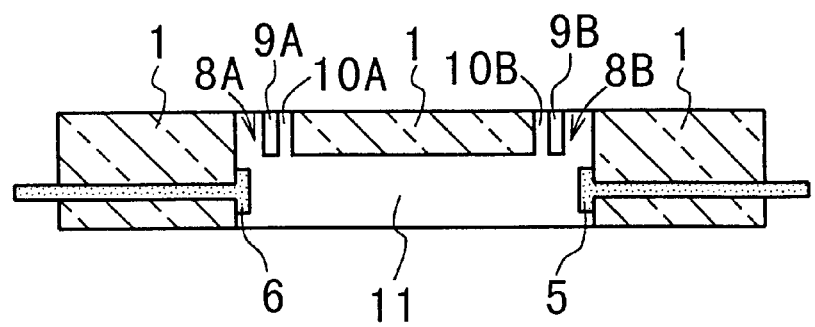
FIG. 4 is a schematic cross-sectional view along the line IV—IV in FIG. 3.

As shown in FIGS. 3 and 4, the cap 1 has a shape of a rectangular plate and is made of quartz. A cavity 11 is formed in the central area of the cap 1. Here, the cavity 11 has a shape of a rectangular parallelepiped. The cavity 11 is defined by a top wall and four side walls. The bottom of the cavity 11 is opened.

In the two side walls of the cavity 11, which are located on the left- and right-hand sides in FIGS. 3 and 4, a positive electrode 5 and a negative electrode 6 are attached to penetrate through the corresponding side walls, respectively. The inner ends of the electrodes 5 and 6 are located in the cavity 11. The outer ends of the electrodes 5 and 6 are protruded from the corresponding side walls, respectively. Each of the electrodes 5 and 6 is made of platinum (Pt).

In the top wall of the cavity 11, which is located on the top in FIG. 4, slits 8A and 8B are formed at left- and right-hand side ends of the cavity 11, respectively. The slits 8A and 8B extend in parallel to each other and are located in the vicinities of the negative and positive electrodes 6 and 5, respectively.

In the slit 8A, two projections 9A are formed to project along the corresponding side wall of the cavity 11. The projections 9A are opposed to one another. Similarly, in the slit 8B, two projections 9B are formed to project along the corresponding side wall of the cavity 11. The projections 9B also are opposed to one another.

Figure 5:
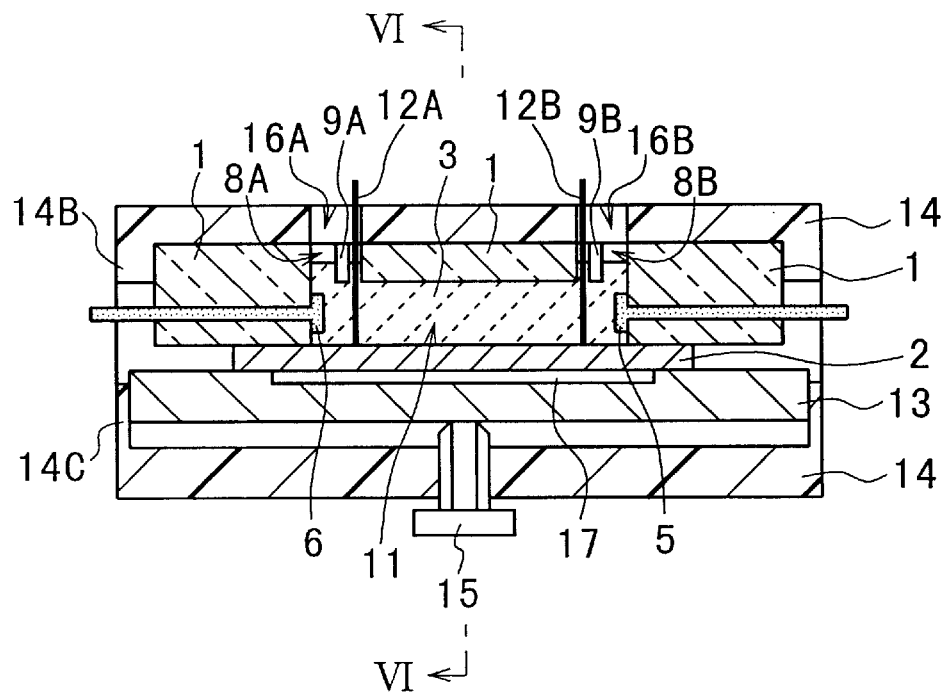
FIG. 5 is a schematic cross-sectional view showing a zeta-potential determining apparatus according to the first embodiment of the present invention, in which the cell member in FIGS. 3 and 4 is incorporated.

As clearly shown in FIG. 5, the two projections 9A and the neighboring end of the top wall of the cavity 11 define a membrane-insertion space 10A. A bubble-barrier membrane 12A is inserted into the space 10A on use. Similarly, the two projections 9B and the neighboring end of the top wall of the cavity 11 define a membrane-insertion space 10B. A bubble-barrier membrane 12B is inserted into the space 10B on use.

The opening bottom of the cavity 11 is closed by a flat and rectangular bottom plate 2 on use, allowing a testing solution 3 to be stored in the cavity 11. Here, the bottom plate 2 is made of quartz.

In this embodiment, the cap 1 is of an integral structure, as shown in FIGS. 3 and 4. However, it may be made up of upper and lower plate-like parts, which are coupled together. The lower part has a rectangular penetrating hole defining the cavity 11. The upper part has two slits defining the slits 8A and 8B. Each of the upper and lower parts may be made of quartz, acrylic plastic, or acrylic plastic coated with quartz.

The cap 1 may be made of any other material through which an irradiated laser beam penetrates.

Figure 6:
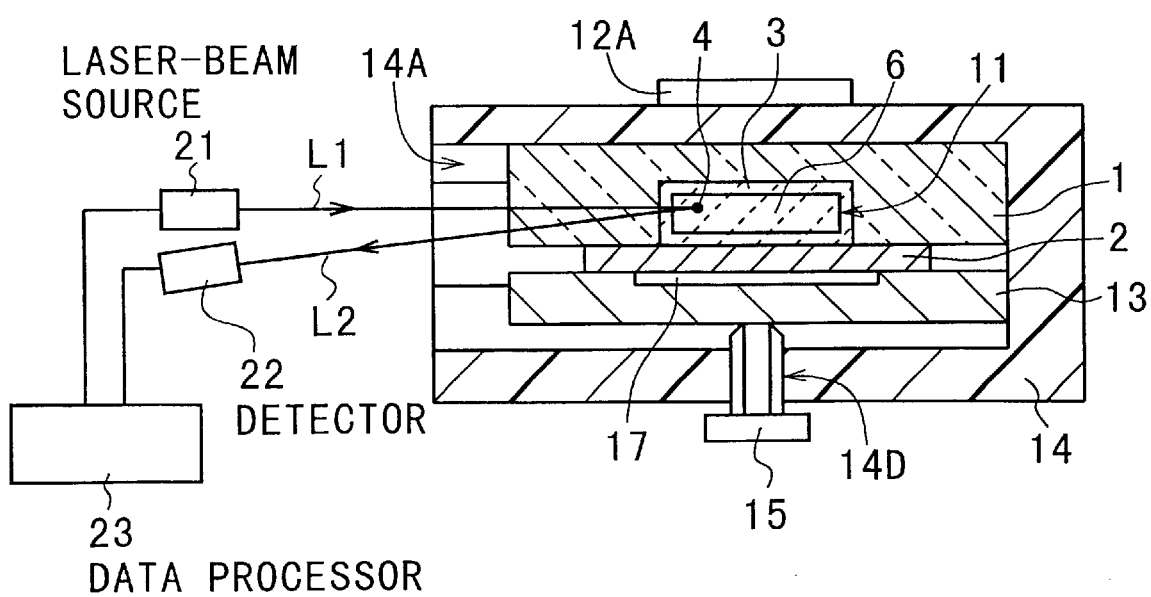
FIG. 6 is a schematic cross-sectional view along the line VI—VI in FIG. 5.

As shown in FIGS. 5 and 6, the bottom plate 2 is set onto the bottom surface of the cap I to close the opening bottom of the cavity 11. The supporting member 13, which is flat and rectangular, is set onto the bottom plate 2. The supporting member 13 is greater in size than the bottom plate 2 and is approximately the same than the cap 1.

The supporting member 13 has a recess 17 on its top surface. The recess 17 has a rectangular plan shape and serves to facilitate the detachment of the member 13 from the bottom plate 2.

The cap 1, the bottom plate 2, and the supporting member 13 (in other words, the cell member and the supporting member 13) constitute a cell assembly.

The cell block 14 has a U-shaped cross section, the front and both sides of which are open. In other words, the block 14 is formed by the top and bottom walls connected by the back wall thereof. The block 14 has an inner space 14A with a shape of a rectangular parallelepiped.

The cell assembly, which is constituted by the cap 1, the bottom plate 2, and the supporting member 13, is designed to be inserted into the inner space 14A of the cell block 14, as shown in FIGS. 5 and 6. The top wall of the block 14 has protruding ends 14B at the right and left sides. The upper ends 14B serve as a guide for the cap 1. The bottom wall of the block 14 has protruding ends 14C at the right and left sides. The ends 14C serve as a guide for the supporting member 13.

The bottom wall of the block 14 has a screwed hole 14D. A screw 15 is inserted into the screwed hole 14D to press the supporting member 13 upward, fixing the cell assembly in the block 14.

The top wall of the cell block 14 has two slits 16A and 163. The slits 16A and 16B are located at positions where the slits 8A and 8B of the cap 1 are entirely overlapped therewith when the cell assembly is inserted and fixed into the block 14, as shown in FIGS. 5 and 6. Thus, the bubble-barrier membranes 12A and 12B may be inserted into the cavity 11 through the overlapped slits SA and 16A and BB and 16B, respectively, as shown in FIG. 5. Also, bubbles generated in the cavity 11 may be discharged to the outside through the overlapped slits 8A and 16A and 8B and 16B, respectively.

Next, the use of the zeta-potential determining apparatus according to the first embodiment is explained below.

First, the bottom plate 2 is attached onto the bottom surface of the cap 1 to close the opening bottom of the cavity 11, and the supporting member 13 is attached onto the bottom surface of the plate 2. Thus, the cell assembly is constituted. Since a sealing member (not shown) is provided between the cap 1 and the bottom plate 2, the leakage of the solution is prevented.

Then, this cell assembly is inserted into the inner space 14A of the cell block 14 through the opening front opening until the back of the assembly is contacted with the back wall of the cell block 14. The assembly is then fixed by fastening the screw 15. Thus, the cavity 11 is prepared for the solution.

Further, the bubble-barrier membranes 12A and 12B are inserted into the spaces 10A and 10B of the cap 1, respectively. The membranes 12A and 12B are held by the corresponding projections 9A and 9B and the top wall of the cap 1. At this stage, the bottoms of the membranes 12A and 12B are contacted with the bottom plate 2. Thus, the neighborhood of the negative electrode 6 is separated from the central region of the cavity 11 by the membrane 12A. Similarly, the neighborhood of the positive electrode 5 is separated from the central region of the cavity 11 by the membrane 12B.

Subsequently, the solution 3 to be measured is supplied to the cavity 11 through the slit 8A or 8B with the use of a thin tube. The solution 3 contains the monitor particles 4 dispersed therein.

As the bubble-barrier membranes 12A and 12B, a filter paper or an ion-exchange membrane may be used. The filter paper or ion-exchange membrane may be inserted as it is or inserted after fixing it to an appropriate frame (not shown) made of Teflon or the like. Preferably, any one of the fluorine-system ion-exchange membranes may be used.

As the solution 3, a mixed solution of a hydrochloric acid and hydrogen peroxide, for example, may be used- As the monitor particles 4, PSL particles with a diameter of 0.5 $\mu$m may be used, for example.

Subsequently, to move the dispersed monitor particles 4 in the solution 3 due to the electrophoresis phenomenon, a dc voltage (for example, 100 V) is applied across the positive and negative electrodes 5 and 6. Because the solution 3 contains hydrogen peroxide, a number of bubbles are generated in the solution 3 in the vicinities of the electrodes 5 and 6. However, the bubble-barrier membranes 12A and 12B located in the vicinities of the corresponding electrodes 5 and 6 prevent the generated bubbles from being diffused toward the central region of the cavity 11 where an incident laser beam L1 is irradiated.

In the state as shown in FIGS. 5 and 6, the bubbles are discharged to the outside through the overlapped slits 8A and 16A and 8B and 16B. Then, an incident laser beam L1 emitted from a laser-beam source 21 is irradiated through the front wall of the cap 1 to the solution 3 in the central region of the cavity 11 between the bubble-barrier membranes 12A and 12B, as shown in FIG. 6.

Figure 2:
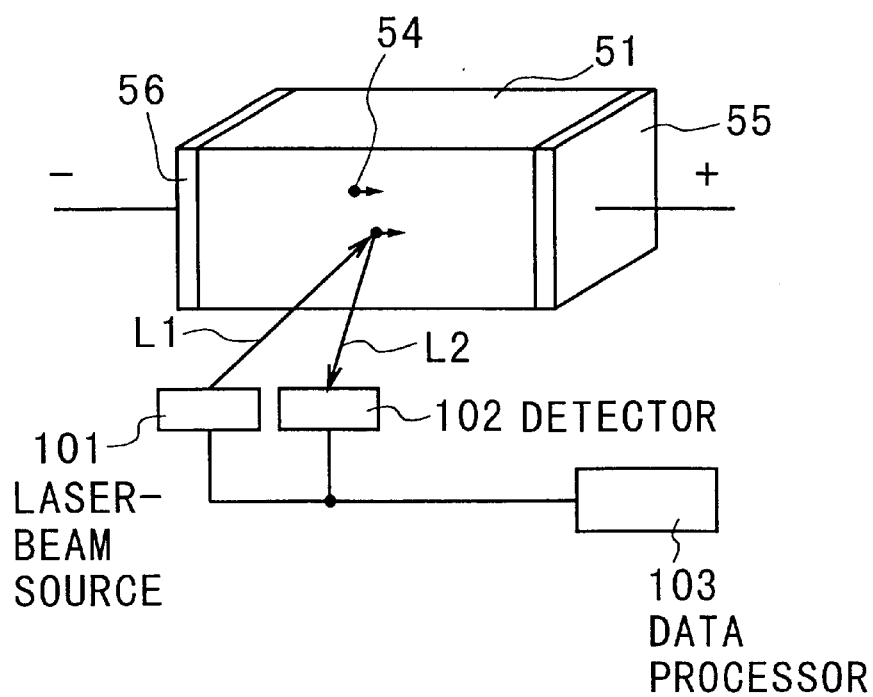
FIG. 2 is a schematic, perspective view showing the zeta-potential determination method using the conventional cell member shown in FIG. 1.

A reflected laser beam L2 by the monitor particles 4 is detected by an optical detector 22. A data processor 23 calculates or determines the mobility of the particles 3 in the same way as that explained in the above conventional apparatus with reference to FIG. 2.

The solution 3 is take out from the cavity 11 through the slit 8B or 8A with the use of a thin tube for a subsequent solution, and the cavity 11 is washed with pure water.

As described above, with the zeta-potential determining apparatus according to the first embodiment, the bubble-barrier membrane 12A is placed in the portion 10A of the cell member in the vicinity of the negative electrode 6 and the bubble-barrier membrane 12B is placed in the portion 10B of the cell member in the vicinity of the positive electrode 5 on use (i.e., on zeta-potential determination). The bubble-barrier membrane 12A has the property of blocking the bubbles generated in the solution 3 in the vicinity of the negative electrode 6 that move toward the positive electrode 5. The bubble-barrier membrane 12B has the property of blocking the bubbles in the solution in the vicinity of the positive electrode 5 that move toward the negative electrode 6.

Accordingly, the bubbles in the solution 3 do not enter the intervening central region between the portions 10A and 10B of the cell member This means that the bubbles are prevented from existing in the central region.

On the other hand, each of the bubble-barrier membranes 12A and 12B has the property of allowing the ions contained in the solution 3 to penetrate through a corresponding one of the bubble-barrier membranes 12A and 12B. Therefore, a sufficient electric current may flow through the solution 3 according to the applied dc voltage, and thus, the monitor particles 4 in the solution 3 may be moved in the solution 3 due to the electrophoresis phenomenon.

This means that a zeta-potential is able to be determined accurately even if the solution 3 has a tendency of generating bubbles due to an applied electric field.

As a result, this zeta-potential determining apparatus according to the first embodiment can be used for monitoring the performance of a cleaning or rinsing solution with a tendency of generating bubbles due to an applied electric field.

Figure 7:
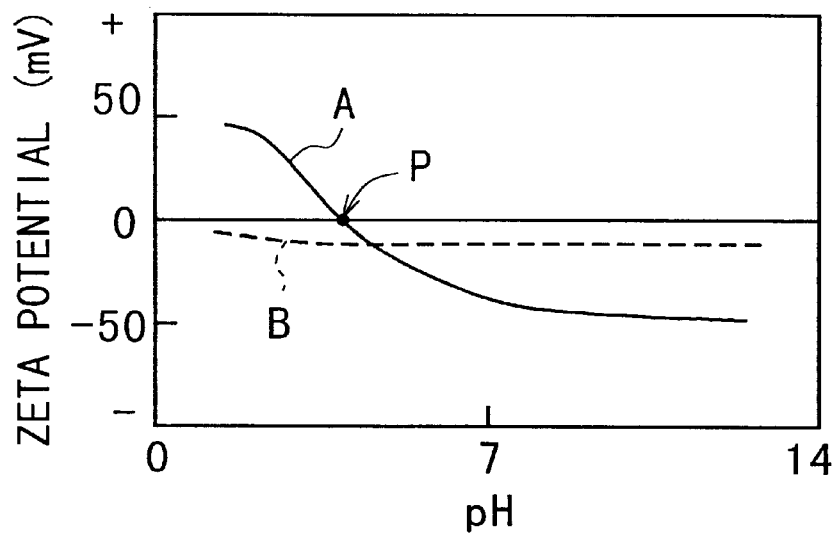
FIG. 7 is a graph indicating the pH dependence of the Zeta potential, which was obtained by the Zeta potential determination using the apparatus according to the first embodiment in FIGS. 3 to 6.

FIG. 7 is a graph indicating the pH dependence of the Zeta potential of the PSL particle in the HPM solution.

The PSL particle has an equipotential point in the acidic region. On the other hand, in general, a negatively charged particle including the PSL particle has a property of representing a positive zeta potential due to the effect of the $H^+$ ions in an acidic solution when the acidity is increased to over a certain value. The point P in FIG. 7 where the zeta potential is changed from a positive value to a negative one is known as the "equipotential point".

Figure 1:
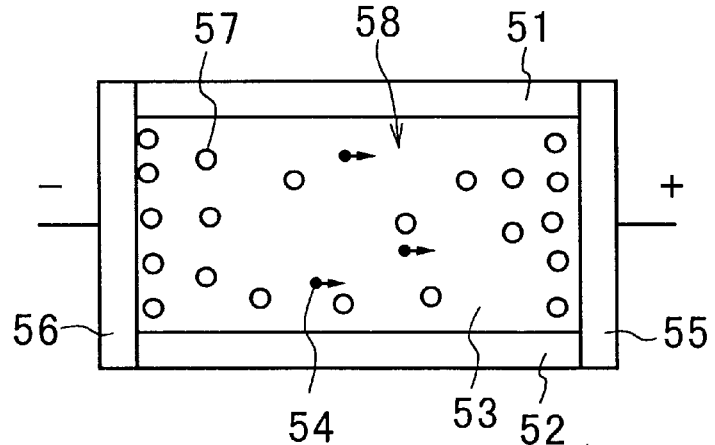
FIG. 1 is a schematic cross-sectional view showing the outline of a conventional cell member of a conventional zeta-potential determining apparatus.

When the conventional determining apparatus shown in FIG. 1 was used, only the result that the zeta potential was practically not changed with the change in pH, as shown with the curve B, was obtained. The basic property for the zeta potential could not be determined.

Contrarily, when the determining apparatus according to the first embodiment was used, the obtained zeta potential revealed the dependency upon the pH, as shown with the curve A in FIG. 7, giving the equipotential point P in the acidic region. Thus, even if hydrogen peroxide was contained in the solution 3, the basic property for zeta potential could be confirmed.

For example, the rectangular cap 1 has a length of 110 mm, a width of 60 mm, and a thickness of 25 mm. The cavity 11 has a size of 50 mm×20 mm×13 mm. Each of the slits 8A and 8B has a width of 1 to 3 mm.

Second Embodiment

Figure 8:
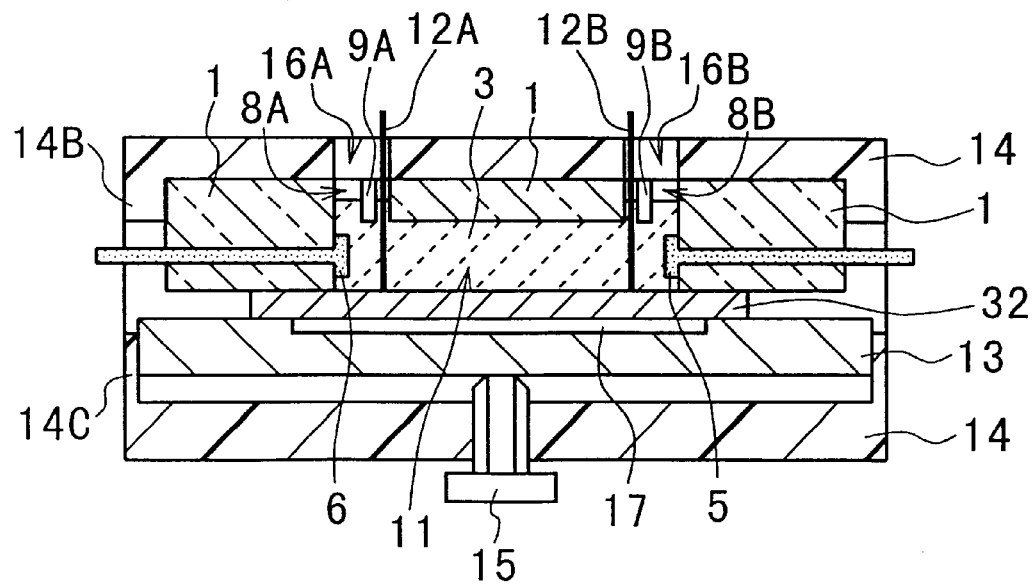
FIG. 8 is a schematic cross-sectional view showing a zeta-potential determining apparatus according to a second embodiment of the present invention, in which a testing sample is used as the bottom plate of the cell member.

A zeta-potential determining apparatus according to a second embodiment of the present invention is shown in FIG. 8. This apparatus has the same configuration as that of the first embodiment in FIGS. 3 to 6, except that a plate-shaped sample 32 to be determined is used as the bottom plate 2. Therefore, the description relating the same configuration is omitted here for the sake of simplification of description by attaching the same reference numerals to the same or corresponding elements in FIG. 8.

As the plate-shaped sample 32, a silicon substrate may be used, for example.

With the zeta-potential determining apparatus according to the second embodiment, the zeta potential at the surface of the plate-shaped sample 32 is determined. The basic principle for determining the mobility of the monitor particle 3 moved by the electrophoresis phenomenon is the same as that in the first embodiment described above. However, unlike the first embodiment, the distribution of the mobility of the monitor particle 4 is determined as a function of the distance from the sample plate 32.

In general, when the sample plate 32 has an electric charge, this electric charge has a great effect on the monitor particles 4 in the vicinity of the sample plate 32, greatly affecting the mobility of the particles 4. The greater the distance from the sample plate 32, the lower the degree of the effect on the monitor particle 4. Thus, the effect of the charge in the sample plate 32 on the mobility of the monitor particles 4 can be determined as the distribution of mobility against distance from the sample plate 32. From the determined distribution of mobility, the amount of charge on the surface of the sample plate 32 can be calculated.

For example, when the zeta potential of the surface of a silicon substrate is determined, the silicon substrate is attached onto the bottom of the cap 1 as the sample plate 32.

Figure 9:
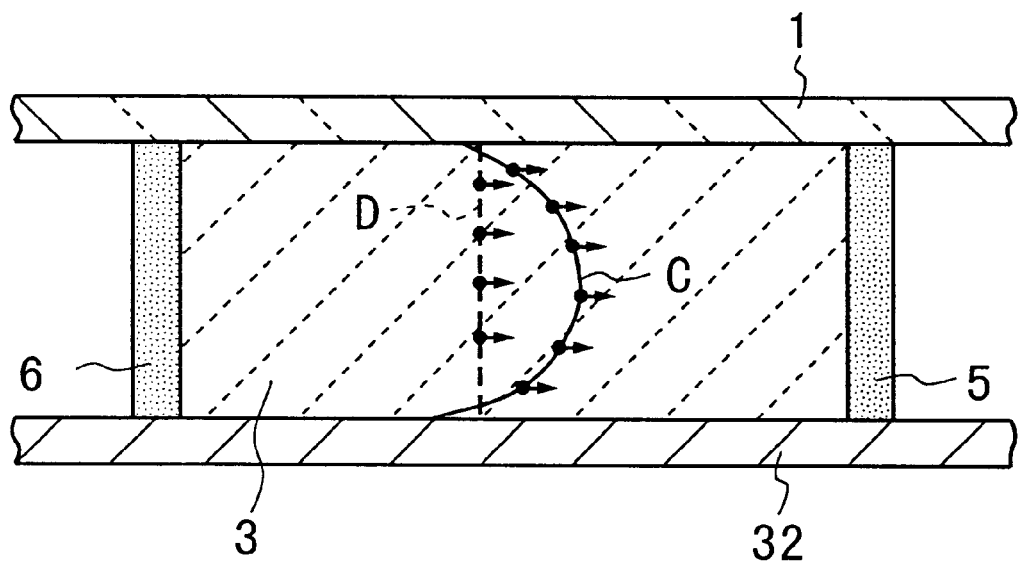
FIG. 9 is a schematic illustration showing the distance dependence of the mobility of the monitor particles from the testing sample, which was obtained by the mobility measurement using the apparatus according to the second embodiment in FIG. 8.

FIG. 9 schematically shows the mobility distribution measured by using the apparatus according to the second embodiment, in which a silicon substrate was used as the sample plate 32 and a HPM of pH was used as the solution 3.

The curves C and D in FIG. 8 represent the result of the mobility distribution of the monitor particles 4 between the silicon substrate 32 at the bottom and the quartz top wall of the cap 1, which was obtained by using the laser beams L1 and L2 in FIG. 6.

When the conventional determining apparatus was used, the bubbles cannot be distinguished from the monitor particles and thus, the distribution curve was almost a straight line as shown with the curve D, and the amount of charge on the surface of the substrate 32 could not be calculated.

Contrarily, when the determining apparatus according to the second embodiment of the present invention was used, filter papers serving as the bubble-barrier membranes 12A and 12B eliminate the effect of the bubbles, allowing the measurement of the monitor particles 4 only. Thus, the distribution as shown with the curve C was obtained, and the amount of charge on the surface of the silicon substrate 32 and the surface zeta potential thereof could be determined.

The above description is on the assumption that a filter paper is used as each of the bubble-barrier membranes 12A and 12B. Since the required properties of the bubble-barrier membranes 12A and 12B is to block off the bubbles, to allow the ions to penetrate, and to make no chemical reaction with the monitor solution 3. Therefore, glass filters and ion-exchange membranes may also be used.

As described above, the zeta potential determining apparatuses according to the first and second embodiments are capable of accurate determination of the zeta potential for a cleaning or rinsing solution that can easily generate bubbles at the electrodes during determination.

Especially for many cleaning solutions containing hydrogen peroxide that are frequently used for cleaning semiconductor substrates, determination of the zeta potential can be made.

Therefore, the cleaning performance of the cleaning and rinsing solutions used in manufacturing of precision industrial products including semiconductors can be more accurately known, and solutions having a higher cleaning or rinsing effect can be used for manufacturing, resulting in an improved yield and reliability.

While the preferred forms of the present invention has been described, it is to be understood that modifications will be apparent to those skilled in the art without departing from the spirit of the invention. The scope of the invention, therefore, is to be determined solely by the following claims.

What is claimed is:

1. A zeta-potential determining apparatus, comprising:

a cell having a cavity that is a parallelepiped with a major axis that is horizontal;

two electrodes at opposing ends of said cavity with a zeta-potential determination area between said two electrodes;

two electrode gas bubble-barriers in said cavity, each of said barriers separating a different one of said electrodes from said zeta-potential determination area and preventing electrode gas bubbles from reaching said zeta-potential determination area;

two vertical slots in an upper surface of said cell that extend into said cavity, each of said barriers being arranged vertically in a respective one of said slots, and wherein said slots are also arranged and constructed to permit escape of the electrode gas bubbles from said cavity though said slots and a laser system selectively illuminating said zeta-potential determination area with a laser light and determining a zeta potential based on a reflection of the laser light.

* * * * *